United States Patent [19]
Akamatsu et al.

[11] Patent Number: 5,773,442
[45] Date of Patent: Jun. 30, 1998

[54] BENZAMIDINE DERIVATIVES AND PHARMACEUTICAL COMPOSITION CONTAINING THEM

[75] Inventors: Seijiro Akamatsu; Yuzo Matsumoto; Masato Ichihara; Tomihisa Kawasaki; Seiji Kaku, all of Ibaraki; Isao Yanagisawa, Tokyo, all of Japan

[73] Assignee: Yamanouchi Pharmaceutical Co., Ltd., Tokyo, Japan

[21] Appl. No.: 875,702

[22] PCT Filed: Feb. 8, 1996

[86] PCT No.: PCT/JP96/00274

§ 371 Date: Aug. 4, 1997

§ 102(e) Date: Aug. 4, 1997

[87] PCT Pub. No.: WO96/24583

PCT Pub. Date: Aug. 15, 1996

[30] Foreign Application Priority Data

Feb. 10, 1995 [JP] Japan ................................ 7-022640
Apr. 6, 1995 [JP] Japan ................................ 7-081426

[51] Int. Cl.⁶ .................... C07D 211/58; C07D 211/60; C07D 401/04; A61K 31/495
[52] U.S. Cl. .................... 514/255; 544/360; 544/365
[58] Field of Search ........................ 544/360, 365; 514/255

[56] References Cited

U.S. PATENT DOCUMENTS 5,442,064 8/1995 Pieper et al. ..................... 544/360

FOREIGN PATENT DOCUMENTS 542 363 5/1993 European Pat. Off. .

WO 93/14077 7/1993 WIPO .

OTHER PUBLICATIONS

Judkins et al., A Versatile Synthesis of Amidines from nitriles via Amidoximes, Synthetic Communications, 26(23), 4351–4367, 1996.

Eldred et al., Orally Active Non–peptide Fibrinogen Receptor (GPIIb/IIIa) Antagonists, J. Med. Chem., 37(23), 3882–5, 1994.

*Primary Examiner*—Mukund J. Shah
*Assistant Examiner*—Deepak R. Rao
*Attorney, Agent, or Firm*—Burgess, Ryan & Wayne

[57] ABSTRACT

Disclosed are benzamidine derivatives of the following general formula (I), salts thereof, hydrates thereof or solvates thereof, and pharmaceutical compositions comprising the derivatives, salts thereof, hydrates thereof or solvates thereof along with pharmaceutically-acceptable carriers.

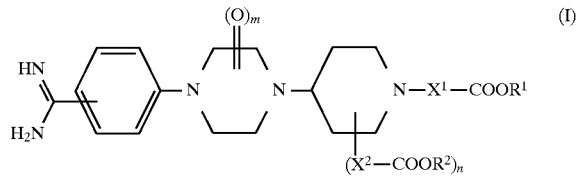

The derivatives and their compositions have GPIIb/IIIa receptor antagonistic activity and are useful for the treatment and prophylaxis of vascular system disorders as medicines for ameliorating ischemic cardiac disorders, adminicula in cardiosurgery operations or in vascular surgery operations, medicines for ameliorating cerebrovascular disorders, and medicines for ameliorating peripheral artery disorders.

20 Claims, No Drawings

BENZAMIDINE DERIVATIVES AND PHARMACEUTICAL COMPOSITION CONTAINING THEM

This application is a 371 of PCT/JP96/00244 filed on Feb. 8, 1996.

TECHNICAL FIELD

The present invention relates to novel benzamidine derivatives or their salts which are useful as medicines, especially as GPIIb/IIIa antagonists, and to pharmaceutical compositions containing such compounds.

BACKGROUND ART

Blood platelets, since their discovery by Donne in 1842 (see C. R. Acad. Sci. (Paris), 14, 336–368, 1842), have been considered, for a long period of time, as components in blood which are necessary for hemostasis. At present, it has been determined that blood platelets not only play the principal part in the hemostatic mechanism of blood but also are multi-functional as participating in the creation of arteriosclerosis, cardiovascular system disorders including thrombotic disorders, cancer metastases, inflammations, rejections after transplants, even immunoreactions and others which are clinically important. Therapies for such thrombotic disorders and ischemic disorders are employed to restore the circulation of the blood by the application of medicines or physical means to patients. Recently, however, the occurrence of clinically problematic phenomena has been found after the restoration of the circulation of the blood, which are such that the blood vessel tissue having endothelial cells therein is damaged, the medicines applied make the adenolysis-coagulation equilibrium of the body unbalanced, etc., with the result that the activation, the adhesion and the aggregation of blood platelets are promoted too much. For instance, it has been determined that, after the circulation of the blood has been restored by thrombolytic therapy using t-PA or the like, the adenolytic ability and the coagulating ability of the restored blood are activated to thereby make the systemic adenolysis-coagulation equilibrium of the body unbalanced. Clinically such causes re-obstruction and is therefore seriously problematic in therapy of the disorders (see J. Am. Coll. Cardiol., 12, 616–623, 1988). On the other hand, a PTCA therapy has been rapidly popularized, with producing good results in some degree, for curing disorders as based on coronary stenosis and aortostenosis, such as stenocardia, myocardial infarction, etc. However, this therapy involves serious problems in that it damages the blood vessel tissue having therein endothelial cells to thereby cause acute coronary obstruction and even re-stenosis in about 30% of cured patients. Blood platelets play the principal part in various thrombotic disorders (e.g., re-obstruction) following such blood circulation-restoring therapy. Therefore, the effectiveness of platelet aggregation inhibitors would be expected for such disorders. However, conventional platelet aggregation inhibitors have not as yet been verified to be satisfactorily effective. GPIIb/IIIa is a platelet membrane glycoprotein which is one of the integrin family (see Blood, 80, 1386–1404, 1992). The integrin bonds to adhesive proteins such as fibrinogen, von Bill Brand factor, etc., while displaying an important function at the terminal in blood platelet aggregation. Monoclonal antibodies to GPIIb/IIIa as well as peptides and others having an RGD sequence have high platelet aggregation inhibiting activity, some of which have already been put into clinical examinations. Non-peptidic, low-molecular GPIIb/IIIa antagonists are described in Japanese Patent Laid-Open Nos. 4-288051 and 6-25227 and are disclosed by Leo et al. (see Journal of Medicinal Chemistry, 35, 4393–4407, 1992). However, these are all for intravenous injection and can be used only at the acute stage of disorders. On the other hand, orally-applicable GPIIb/IIIa antagonists are disclosed in European Patent Laid-Open No. 542363, but their peroral activity cannot be said to be satisfactory. Therefore, peroral GPIIb/IIIa antagonists with definite effect are much desired. The compounds of the present invention are novel benzamidine derivative which are different from the compounds described in the above-mentioned patent specifications in their structure and especially display strong GPIIb/IIIa antagonistic activity even in oral administration.

DISCLOSURE OF THE INVENTION

The present inventors have assiduously studied the above-mentioned compounds that display GPIIb/IIIa antagonistic activity and, as a result, have created novel benzamidine derivative and found that the derivative have good GPIIb/IIIa antagonistic activity. On the basis of this finding, they have completed the present invention.

Specifically, the present invention relates to benzamidine derivative of the following general formula (I) or their salts, as well as pharmaceutical compositions comprising such compounds along with pharmaceutically-acceptable carriers.

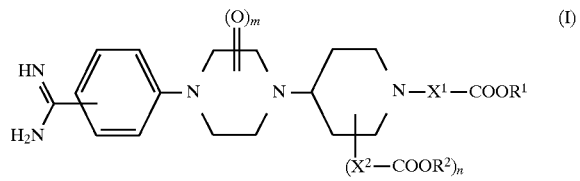

wherein $R^1$ and $R^2$ are the same or different and each represents a hydrogen atom or an ester residue;
X1 represents a lower alkylene group;
$X^2$ represents a single bond or a lower alkylene group;
m represents 0, 1 or 2;
n represents 0 or 1, provided that n=1 when m=0.

The compounds of the present invention are structurally characterized in that the piperidine ring has two carboxylic acid residues thereon and/or the piperazine ring has one or two oxo groups thereon, and the compounds have good peroral and lasting activity due to the characteristic structure.

Preferred compounds among the compounds of the present invention of the above general formula (I) are:

the benzamidine derivatives, salts thereof, hydrates thereof, or solvates thereof, wherein $R^1$ and $R^2$ are the same or different and each represents a hydrogen atom, or an ester residue selected from a lower alkyl group, a lower alkenyl group, a lower alkynyl group, a halogeno-lower alkyl group, a cycloalkyl group, a phenyl group, a naphthyl group, an indolyl group, a benzyl group, a lower alkoxy-benzyl group, a nitrobenzyl group, a benzhydryl group, a lower alkoxy-benzhydryl group, a lower alkanoyloxy-lower alkyl group, a lower alkenoyloxy-lower alkyl group, a lower alkanoyl-lower alkyl group, a lower alkenoyl-lower alkyl group, a lower alkoxy-lower alkanoyloxy-lower alkyl group, a lower alkoxy-lower alkenoyl-lower alkyl group, a lower alkoxy-lower alkyl group, a lower alkoxy-lower alkoxy-lower alkyl group, a cycloalkyloxycarbonyloxy-lower alkyl group, a lower alkoxycarbonyloxy-lower alkyl group, a lower alkoxy-lower alkoxycarbonyloxy-lower alkyl group, a benzoyloxy-lower alkyl group, a di-lower alkylamino-lower alkyl group, a 2-oxotetrahydrofuran-5-yl group, a 2-oxo-5-alkyl-1,3 dioxolen-4-ylmethyl group, a tetrahydrofuranyl-carbonyloxymethyl group or a 3-phthalidyl group;

the benzamidine derivatives, salts thereof, hydrates thereof, or solvates thereof, wherein $R^1$ and $R^2$ are the same or different and each represents a hydrogen atom, or an ester residue selected from a lower alkyl group, a lower alkenyl group, a halogeno-lower alkyl group, a lower alkoxy-lower alkyl group, a lower alkoxycarbonyloxy-lower alkyl group, a phenyl group, a benzyl group or a lower alkoxy-benzyl group;

the benzamidine derivatives, salts thereof, hydrates thereof, or solvates thereof, wherein $R^1$ and $R^2$ are the same or different and each represents a hydrogen atom or a lower alkyl group;

the benzamidine derivatives, salts thereof, hydrates thereof, or solvates thereof, wherein m=0 and n=1;

the benzamidine derivatives, salts thereof, hydrates thereof, or solvates thereof, wherein m=1 or 2 and n=0.

DESCRIPTION OF THE PREFERRED EMBODIMENTS

The compounds (I) of the present invention are described in detail hereinunder.

Unless otherwise specifically indicated, the terminology "lower" as referred to herein for the definitions of the general formulae given herein is directed to a linear or branched carbon chain having from 1 to 6 carbon atoms.

In formula (I), therefore, the "lower alkylene group" represented by $X^1$ and $X^2$ is suitably a linear or branched alkylene group having from 1 to 6 carbon atoms, which concretely includes a methylene group, an ethylene group, a methylmethylene group, a trimethylene group, a propylene group, a tetramethylene group, a pentamethylene group, a hexamethylene group, a pentylmethylene group, a butylmethylmethylene group, an ethylpropylmethylene group, etc. Above all, preferred are linear alkylene groups having from 1 to 3 carbon atoms, especially methylene and ethylene groups.

The compounds (I) where $R^1$ and/or $R^2$ are/is ester residue(s) are active and can be medicines by themselves. These are also useful as prodrugs which are metabolized in vivo to be converted into active, free carboxylic acids, or are useful as intermediates for producing the corresponding free carboxylic acids. Therefore, the "ester residues" for $R^1$ and $R^2$ include ester residues which can be hydrolyzed by metabolism in vivo and/or can be carboxyl-protecting groups and which are well known by those skilled in the art. As such ester residues, usable are ordinary ester residues which include, for example, a lower alkyl group, a lower alkenyl group, a lower alkynyl group, a halogeno-lower alkyl group, a cycloalkyl group, a phenyl group, a naphthyl group, an indolyl group, a benzyl group, a lower alkoxy-benzyl group, a nitrobenzyl group, a lower alkoxy-benzhydryl group, a benzhydryl group, a lower alkanoyloxy-lower alkyl group, a lower alkenoyloxy-lower alkyl group, a lower alkanoyl-lower alkyl group, a lower alkenoyl-lower alkyl group, a lower alkoxy-lower alkanoyloxy-lower alkyl group, a lower alkoxy-lower alkenoyloxy-lower alkyl group, a lower alkoxy-lower alkyl group, a lower alkoxy-lower alkoxy-lower alkyl group, a cycloalkyloxycarbonyloxy-lower alkyl group, a lower alkoxycarbonyloxy-lower alkyl group, a lower alkoxy-lower alkoxycarbonyloxy-lower alkyl group, a benzoyloxy-lower alkyl group, a di-lower alkylamino-lower alkyl group, a 2-oxotetrahydrofuran-5-yl group, a 2-oxo-5-alkyl-1,3-dioxolen-4-ylmethyl group, a tetrahydrofuranylcarbonyloxymethyl group, a 3-phthalidyl group, etc. Of these, preferred are a lower alkyl group, a lower alkenyl group, a halogeno-lower alkyl group, a lower alkoxy-lower alkyl group, a lower alkoxycarbonyloxy-lower alkyl group, a phenyl group, a benzyl group and a lower alkoxy-benzyl group, and especially preferred is a lower alkyl group.

The "lower alkyl group" as referred to herein is a linear or branched alkyl group having from 1 to 6 carbon atoms, including, for example, a methyl group, an ethyl group, a propyl group, an isopropyl group, a butyl group, an isobutyl group, a sec-butyl group, a tert-butyl group, a pentyl group, a hexyl group, a 1-ethyl-2-methylpropyl group, etc. Especially preferred are a methyl group and an ethyl group. The above-mentioned lower alkyl groups as substituted by various substituents are the above-mentioned lower alkyl groups where any one or more hydrogen atoms is/are substituted by one or more substituents.

The "lower alkenyl group" is a linear or branched alkenyl group having from 2 to 6 carbon atoms, including, for example, a vinyl group, an allyl group, a 1-propenyl group, an isopropenyl group, a 1-butenyl group, etc.

The "lower alkynyl group" is a linear or branched alkynyl group having from 2 to 6 carbon atoms, including, for example, an ethynyl group, a 1-propynyl group, a 2-propynyl group, a 1-butynyl group, etc.

The "halogeno-lower alkyl group" corresponds to the above-mentioned lower alkyl group where one or more hydrogen atoms is/are substituted by halogen atom(s) selected from a fluorine atom, a chlorine atom, a bromine atom and a iodine atom. This includes, for example, a chloromethyl group, a bromomethyl group, a fluoromethyl group, a trifluoromethyl group, a 1,1-dichloroethyl group, a 1-chloro-2-bromoethyl group, etc.

The "cycloalkyl group" and the "cycloalkyl moiety" in the "cycloalkyloxycarbonyloxy-lower alkyl group" each are a cycloalkyl group having from 3 to 8 carbon atoms, including, for example, a cyclopropyl group, a cyclobutyl group, a cyclopentyl group, a cyclohexyl group, a cycloheptyl group, etc.

The "lower alkoxy moiety" in any of the "lower alkoxy-benzyl group", the "lower alkoxy-benzhydryl group", the "lower alkoxy-lower alkanoyloxy-lower alkyl group", the "lower alkoxy-lower alkyl group", the "lower alkoxy-lower alkoxy-lower alkyl group", the "lower alkoxycarbonyloxy-lower alkyl group" and the "lower alkoxy-lower alkoxycarbonyloxy-lower alkyl group" is preferably a lower alkoxy group having the above-mentioned lower alkyl group as its alkyl moiety and includes, for example, a methoxy group, an ethoxy group, a propoxy group, an isopropoxy group, a butoxy group, an isobutoxy group, a sec-butoxy group, a tert-butoxy group, a pentyloxy amyloxy) group, a hexyloxy group, etc. Especially preferred are a methoxy group and an ethoxy group.

The "lower alkanoyl moiety" in any of the "lower alkanoyl-lower alkyl group", the "lower alkanoyloxy-lower alkyl group" and the "lower alkoxy-lower alkanoyloxy-lower alkyl group" is a lower acyl group with from 2 to 6 carbon atoms as derived from a saturated aliphatic carboxylic acid and preferably includes, for example, an acetyl group, a propionyl group, a butyryl group, a valeryl group, a hexanoyl group, etc.

The "lower alkenyl moiety" in any of the "lower alkenoyl-lower alkyl group", the "lower alkenoyloxy-lower alkyl group" and the "lower alkoxy-lower alkenoyloxy-lower alkyl group" is an alkenoyl group having from 3 to 6 carbon atoms and includes, for example, an acryloyl group, a crotonoyl group, a maleoyl group, etc.

The "di-lower alkylamino moiety" in the "di-lower alkylamino-lower alkyl group, corresponds to the above-mentioned lower alkyl group as di-substituted by amino groups, and is a symmetric or asymmetric di-lower alkylamino group including, for example, a dimethylamino group, a diethylamino group, an ethylmethylamino group, a methylpropylamino group, etc.

Of the compounds (I) of the present invention, preferred are those with m=0 and n=1 of the following general formula (Ia) and those with m=1 or 2 and n=0 of the following general formula (Ib):

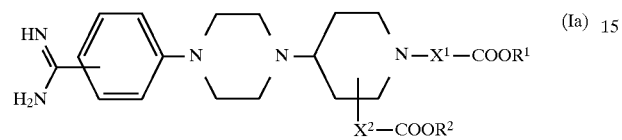

where the symbols have the same meanings as above.

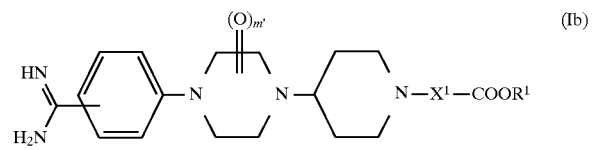

where $X^1$ and $R^1$ have the same meanings as above; and m' represents 1 or 2.

Preferred examples of the compounds of the present invention are mentioned below.

4-[4-(4-Amidinophenyl)-1-piperazinyl]-1,3-piperidine-diacetic acid, its optically-active forms, salts thereof, hydrates thereof and solvates thereof.

4-[4-(4-Amidinophenyl)-2,5-dioxo-1-piperazinyl]-1-piperidine-acetic acid, its optically-active forms, salts thereof, hydrates thereof and solvates thereof.

4-[4-(4-Amidinophenyl)-3-oxo-1-piperazinyl]-1-piperidine-acetic acid, its optically-active forms, salts thereof, hydrates thereof and solvates thereof.

The compounds (I) of the present invention may have at least two asymmetric carbon atoms, depending on the skeletal piperidinyl group and its substituent (group of —$X^2$—$COOR^2$). Further depending on the other substituents, the compounds (I) may have additional asymmetric carbon atom(s). The compounds of the present invention may exist in the form of optical isomers, depending on these asymmetric carbon atoms. In addition, they may exist in the form of tautomeric isomers depending on the carbonyl groups in the substituents and also in the form of geometric isomers depending on the double bonds therein. The present invention encompasses all isolated isomers and their mixtures.

The compounds (I) of the present invention may be formed into salts. As preferred salts, for example, mentioned are alkali metal or alkaline earth metal salts such as sodium salts, potassium salts, calcium salts; hydrohalides such as hydrofluorides, hydrochlorides, hydrobromides, hydroiodides; salts with inorganic acids, such as carbonates, nitrates, perchlorates, sulfates, phosphates, etc.; lower alkylsulfonates such as methanesulfonates, trifluoromethanesulfonates, ethanesulfonates; arylsulfonates such as benzenesulfonates, p-toluenesulfonates; salts with organic acids, such as fumarates, succinates, citrates, tartrates, oxalates, maleates, etc.; salts with amino acids, such as glutamates, aspartates.

In addition, the present invention also encompasses hydrates and pharmaceutically-acceptable solvates of compounds (I) as well as polymorphic isomers of compounds (I), etc.

Needless-to-say, the present invention is not limited to only the compounds of the examples to be mentioned hereinafter but encompasses all benzamidine derivative of formula (I) and their pharmaceutically-acceptable salts.
(Production Methods)

The compounds (I) of the present invention can be produced according to various methods. Some typical methods for producing compounds (I) are mentioned below.

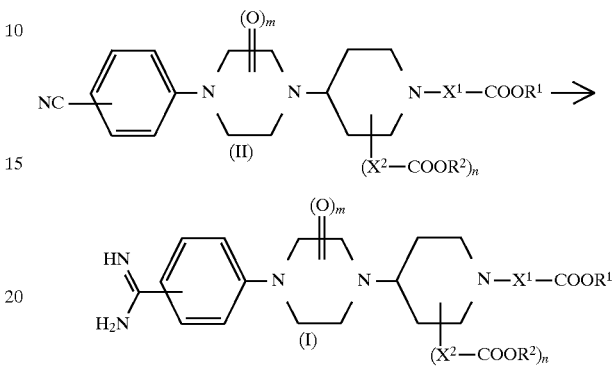

wherein $R^1$, $R^2$, m, n, $X^1$ and $x^2$ have the same meanings as above.

Compounds (I) with an amidino group can be produced according to any of the following methods (i), (ii) and (iii).

(i) Method of converting a nitrile into an imidate followed by condensing it with an amine:

A nitrile compound (II) is reacted with an alcohol such as methanol, ethanol or the like in the presence of a hydrogen chloride gas at from −40° C. to 0° C. to give an imidate, which is then reacted with an amine or amine salt such as ammonia, ammonium carbonate, ammonium chloride, ammonium acetate or the like. As the solvent for the reaction, usable is any of methanol, ethanol, acetone, tetrahydrofuran, etc.

(ii) Method of converting a nitrile into a thioamide and then into a thioimidate followed by condensing it with an amine:

A nitrile compound (II) is reacted with hydrogen sulfide in the presence of an organic base such as methylamine, triethylamine, pyridine, picoline or the like to obtain a thioamide compound. Such a thioamide compound can also be obtained by reacting a nitrile compound (II) with O,O-diethyl dithiophosphate in the presence of hydrogen chloride.

The thus-obtained thioamide compound is then reacted with a lower alkyl halide such as methyl iodide, ethyl iodide or the like to give a thioimidate, which is then reacted with an amine or amine salt such as ammonia, ammonium carbonate, ammonium chloride, ammonium acetate or the like. As the solvent for the reaction, usable is any of methanol, ethanol, acetone, tetrahydrofuran, ethyl acetate, etc. (iii) Method of directly adding an amine, amine salt, metal amide or Grignard reagent to a nitrile:

A reagent such as ammonia, ammonium chloride with ammonia, ammonium thiocyanate, alkylammonium thiocyanate, MeAl(Cl)NH$_2$, NaNH$_2$, (CH$_3$)$_2$NMgBr or the like is added to a nitrile compound (II). Addition of a catalyst of a base such as sodium hydride or the like or an acid such as aluminium chloride, p-toluenesulfonic acid or the like to the reaction system often noticeably accelerates the reaction. The reaction may be conducted with cooling, or at room temperature, or under heat.

Other Production Methods:

Carboxylic acid compounds of formula (I) where $R^1$ and/or $R^2$ are/is hydrogen atom(s) can be obtained by dissolving the corresponding ester compounds of formula (I) in suitable solvents followed by subjecting them to ordinary hydrolysis under basic conditions, acidic conditions or neutral conditions.

Depending on the conditions for the hydrolysis, carboxylic acid compounds of formula (I) where one of $R^1$ and $R^2$ is a hydrogen atom can be obtained. For example, an diester compound of formula (I) in which one ester residue is easily hydrolyzable under acidic conditions (for example, tert-butyl group or the like) and the other ester residue is easily hydrolyzable under basic conditions (for example, methyl ester, ethyl ester or the like) is hydrolyzed under selected conditions (acidic or basic conditions), whereby only one of the two ester residues is selectively hydrolyzed.

If desired, carboxylic acid compounds (I) can be esterified to obtain desired esters. The esterification can be effected in any ordinary manner under suitably selected conditions.

Compounds (I) of the present invention where $R^1$ and/or $R^2$ are/is ester residue(s) can also be obtained by interest-erification with suitable alcohols. For example, a large excessive amount of an alcohol is used for the interesterification to be conducted in the presence of an acid or a base or any other catalyst (for example, titanium (IV) alkoxide) or the other alcohols to be formed during the reaction are removed out of the reaction system, thereby shifting the equilibrium of the reaction toward the system of producing the desired ester compound.

(Methods for Producing Compounds of Raw Materials)

Next, methods for producing compounds to be used as raw materials for the compounds (I) of the invention are mentioned below.

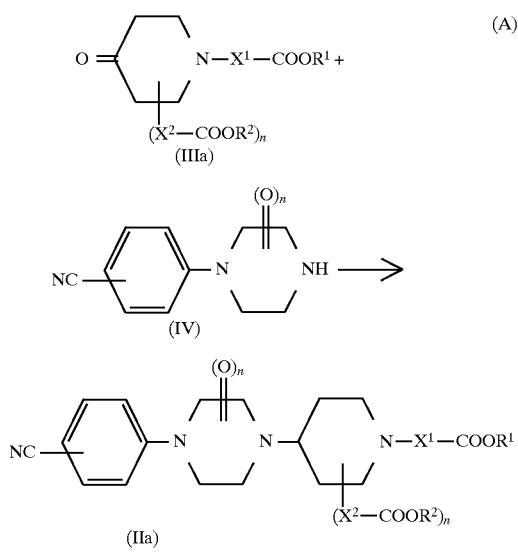

wherein $R^1$, $R^2$, $X^1$, $X^2$, m and n have the same meanings as mentioned above.

A compound (IIa) is obtained by dissolving a compound (IIIa) in a suitable solvent followed by reacting it with an amine compound (IV) to give a Schiff base, which is then reduced. The Schiff base is reduced after having been isolated or without being isolated.

The solvent is an organic solvent inert to the reaction, including, for example, benzene, toluene, methanol, acetic acid, etc.

The reaction is conducted in such a way that a compound (IIIa) is reacted with a reaction-corresponding amount of an amine compound (IV) or, alternatively, a somewhat excessive amount, over the other, of one of these compounds is reacted with the other, preferably in the presence of an acid catalyst such as p-toluenesulfonic acid, adipic acid, oxalic acid, pyridine hydrochloride, acetic acid or the like.

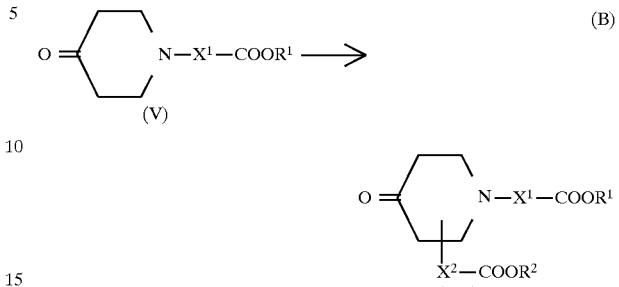

wherein $R^1$, $R^2$, $X^1$ and $X^2$ have the same meanings as above.

A compound (IIIb) is obtained by dissolving a compound (V) in a suitable solvent followed by reacting it with a suitable secondary amine to give an enamine, which is then reacted with an alkyl acrylate (such as methyl acrylate) or a halogenated aliphatic carboxylate (such as ethyl bromoacetate). The enamine may be or may not be isolated before the reaction.

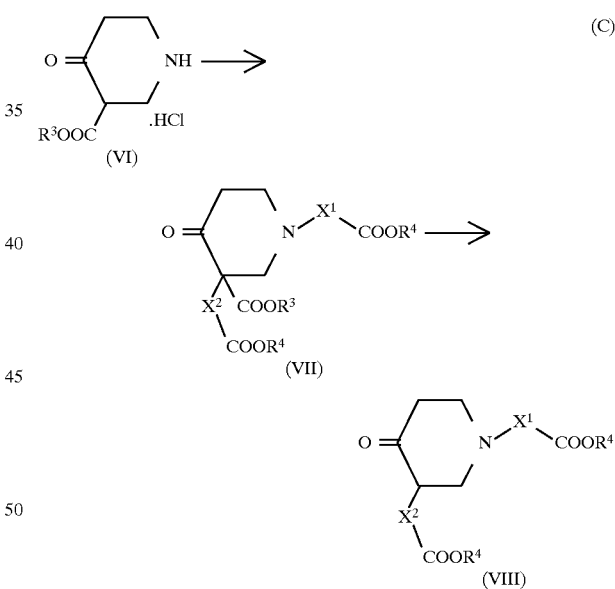

wherein $X^1$ and $X^2$ have the same meanings as above; and $R^3$ and $R^4$ are the same or different and each represents an ester residue.

A compound of formula (VIII) is obtained by reacting a carboxylic acid (VI) with a halogenated aliphatic carboxylate (such as ethyl bromoacetate) in the presence of a base (such as potassium carbonate) to give a compound (VII), which is then de-alkoxycarbonylated under suitable conditions.

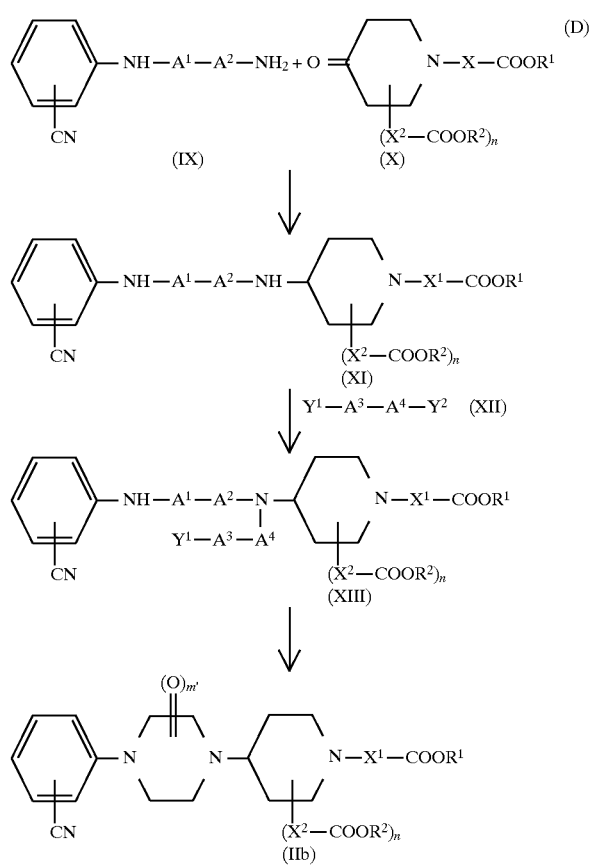

wherein one or two of $A^1$ to $A^4$ is/are carbonyl group(s), while the others are methylene groups; $Y^1$ represents a releasable group, such as a halogen atom, a hydroxyl group, a lower alkoxy group, a phenoxy group, an imidazolyl group, an allylsulfonyloxy group, a releasable group of an active carboxylic acid derivative or the like; $Y^2$ represents a releasable group such as that for $Y^1$ or represents a hydrogen atom; and $X^1$, $X^2$, $R^1$, $R^2$, $m^1$ and n have the same meanings as above.

A compound (IX) is reacted with a compound (X) to give a compound (XI) in the same manner as in the above-mentioned method (A).

The solvent and the catalyst to be used for the reaction and the conditions for the reaction are the same as those in the method (A).

A compound (XIII) is obtained from the compound (XI) according to any of the following reaction processes (1) to (3):

(1) A compound (XI) is reacted with an alkyl derivative (XII) where $Y^2$ is a releasing group of $Y^1$, and $A^4$ is a methylene group.

This reaction may be conducted according to ordinary N-alkylation. Briefly, a compound (XI) is reacted with a reaction-corresponding amount of a compound (XII) in an inert solvent with stirring while cooling or under heat. To promote the reaction, it is desirable to add a base (for example, an inorganic base such as potassium carbonate, sodium carbonate, sodium hydride or the like, or an organic base such as triethylamine or the like) to the reaction system.

(2) A compound (XI) is reacted with a carboxylic acid derivative (XII) where $Y^2$ is a releasable group of $Y^1$, and $A^4$ is a carbonyl group.

Accordingly, an amide compound (XIII) is obtained by acylating a carboxylic acid or its active derivative of formula (XII) with an amine (XI) in a suitable solvent.

The active carboxylic acid derivative to be used in the reaction includes active esters to be obtained by reacting a free carboxylic acid with a phenol compound such as p-nitrophenol or the like, or with an N-hydroxyamine compound such as N-hydroxysuccinimide, 1-hydroxybenzotriazole or the like; mixed acid anhydrides to be obtained by reacting a free carboxylic acid with a monoalkyl carbonate or an organic acid, and mixed phosphoryl anhydrides to be obtained by reacting a free carboxylic acid with diphenylphosphoryl chloride and N-methylmorpholine; acid azides to be obtained by reacting an ester with hydrazine or an alkyl nitrite; acid halides such as acid chlorides, acid bromides, etc.; symmetric acid anhydrides, etc.

An amide compound (XIII) is also obtained by acylating a carboxylic acid (XII) with an amine (XI) in the presence of a condensing agent in a suitable solvent. The condensing agent to be used in the reaction is preferably N,N-dicyclohexylcarbodiimide (DCC), 1-ethyl-3-(3-(N,N-dimethylamino)propyl)carbodiimide, carbonyldiimidazole, diphenylphosphorylazide (DPPA), diethylphosphorylazide or the like.

(3) A compound (XI) is reacted with an aldehyde derivative (XII) where $Y^2$ is a hydrogen atom, and $A^4$ is a carbonyl group.

Accordingly, a compound (XIII) is obtained by dissolving an aldehyde derivative (XII) in a suitable solvent, reacting it with an amine (XI) and thereafter reducing the iminium ion produced in the previous step. For the reaction solvent, the reducing agent and the reaction conditions, referred to are those for the above-mentioned method (A).

To obtain a (di)oxopiperazine compound (IIb) by cyclizing the precursor (XIII) as produced in the above, the precursor (XIII) is treated in a suitable solvent in the absence or presence of a suitable catalyst. This is conducted with cooling with ice or at room temperature or under heat.

The compounds of the present invention as produced in the manner mentioned above are isolated and purified, either directly as their free forms or after having been formed into their salts by ordinary salt-formation. In the latter case, the compounds are obtained as their salts. The isolation and purification of the compounds can be conducted by any ordinary chemical operation which includes, for example, extraction, concentration, distillation, crystallization, filtration, recrystallization, chromatography, etc.

INDUSTRIAL APPLICABILITY

The compounds of the present invention have platelet aggregation-inhibiting activity as orally-applicable GPIIb/IIIa receptor antagonists and are therefore useful as medicines for ameliorating ischemic cardiac disorders (anxiety stenocardia, acute myocardial infarction, and also for prophylaxis of the secondary complications following these, postoperative re-obstruction and re-stenosis following coronary artery bypass or PTCA, as well as for promotion of coronary thrombolysis and prophylaxis of re-obstruction following coronary thrombolysis, etc.); as adminicula in cardiosurgery operations or in vascular surgery operations; as medicines for ameliorating cerebrovascular disorders (transient ischemic attack (TIA), cerebral infarction, subarachnoid hemorrhage (vascular twitch), etc.); and as medicines for ameliorating peripheral artery disorders (chronic arterial obstruction, etc.).

Since the compounds of the present invention have especially excellent peroral absorbability and are therefore useful as medicines for ameliorating the above-mentioned disorders not only by parenteral administration such as, for example, intravascular injection but also by peroral administration. In addition, since the pharmaceutical effects of the compounds of the present invention last a long time, the clinical usefulness of the compounds is high. Moreover, the toxicity of the compounds of the present invention is much lower than that of conventional compounds having similar structures.

The pharmaceutical effects including a platelet aggregation-inhibiting effect of the compounds of the present invention have been confirmed by the following test methods:

Bonding of fibrinogen to pure GPIIb/IIIa:

GPIIb/IIIa was purified according to a Fitzgerald et al's method. Fibrinogen was biotinated with NHS-LC-Biotin (manufactured by Pierce Co.).

The pure GPIIb/IIIa was added to TBS (20 mM Tris-HCl, pH 7.4, 150 mM NaCl, 1 mM $CaCl_2$, 1 mM $MgCl_2$) at one µg/ml. 100 µl of the resulting solution was put into a 96-well plate (MaxiSorp™, manufactured by Nunc Co.) and left at 4° C. overnight. The plate was washed once with TBS, and 20 µl of 1% BSA/TBS was added thereto and left at 37° C. for one hour. After the solution was removed, a sample compound to be tested and the biotinated fibrinogen were added to the plate and reacted at 37° C. for 3 hours. Then, the plate was washed three times with 0.01% Tween 20/TBS. Streptavidin-biotinated horseradish peroxidase complex (manufactured by Amersham Co.) as diluted with 0.1% BSA/TBS to a 1/1000 dilution was added thereto in portions of 100 µl each and reacted at room temperature for 30 minutes. This was washed three times with 300 µl of T-TBS. Then, this was stained with 100 µl of a solution of 2,2'-azidobis-3-ethylbenzothiazoline-6-sulfonic acid (manufactured by Bio Rad Co.) as added thereto, and its absorbance at 414 nm was measured with a microplate reader.

As a result of the above-described test regarding bonding of fibrinogen to pure GPIIb/IIIa, the compound of the present invention showed excellent bonding inhibition. The compound of Example 8 showed $IC_{50}$ of 8.4 nM, and the compound of Example 16 showed $IC_{50}$ of 10.4 nM. The compound of Example 15 of the above-described prior art reference European Patent Laid-Open No. 542363 (hereinafter, referred to as a prior art compound) showed $IC_{50}$ of 68.8 nM.

Ex vivo platelet aggregation-inhibiting activity in cynomolgus monkeys:

Cynomolgus monkeys that had been lightly anesthetized by intramuscular administration of ketamine hydrochloride were fixed on a work-bench, and a sample compound of the present invention as dissolved in 2 ml of dissolved water was forcedly administered into its stomach via a stomach tube at a dose of 3 mg/kg. Before the administration and after the administration at a predetermined period of time, 3 ml (containing 1/10 times by volume of sodium citrate) of the blood was collected from the animal through its femoral vein. From the blood was obtained platelet-rich-plasma (PRP) of 300,000/µl, according to the De Marco et al's method (see J. clin. Invest., 77, 1272–1277, 1988). The PRP was adjusted at $3\times10^8$/ml with an automatic blood cell counter (MEK-5158 Model, produced by Nihon Koden Co.) before use. Added thereto were 20 µM of ADP and 10 µg/ml of bovine tendon-derived collagen (produced by Niko Bioscience Co.) as triggers, whereby the aggregation of the platelets was caused in the PRP. The degree of the aggregation of the platelets was measured with a platelet aggregation meter (NBS Hematracer 801, produced by Niko Bioscience Co.). The platelet aggregation-inhibiting activity of the tested compound was represented by the inhibition percentage (%) relative to the maximum aggregation percentage of each animal before the addition of the compound thereto.

The results of ex vivo platelet aggregation-inhibiting activity test in cynomolgus monkeys are shown in Table 1.

| Compound | platelet aggregation-inhibition ratio (%) | | | | | |
| --- | --- | --- | --- | --- | --- | --- |
|  | 2 hours after | 4 hours after | 6 hours after | 9 hours after | 12 hours after | 24 hours after |
| Example 8 | 57 ± 20 | 98 ± 1.0 | 98 ± 1.2 | 81 ± 19 | 100 ± 0 | 24 ± 9.1 |
| Example 18 | 86 ± 8.4 | 98 ± 0.9 | 75 ± 25 | 97 ± 1.7 | 99 ± 0.7 | 34 ± 11 |
| Prior Art Compound | 37 ± 28 | 93 ± 6.2 | 43 ± 27 | 14 ± 8.9 | 7.7 ± 3.9 | 2.3 ± 1.2 | mean ± SEM (n = 3)

As a result of the above ex vivo platelet aggregation-inhibiting activity test in cynomolgus monkeys, the compounds of the present invention showed sufficient platelet aggregation inhibition ratio even at 12 hours after the oral administration, in comparing the prior art compound.

As a result of the pharmaceutical tests mentioned above, it has been verified that the compounds of the present invention inhibit the binding of fibrinogen to human platelets and therefore have good platelet aggregation-inhibiting activity, that the compounds have good peroral absorbability and that the pharmaceutical effects of the compounds last a long time.

Pharmaceutical compositions comprising one or more of the compounds and their salts of the present invention as the active ingredient can be formulated along with carriers, vehicles and other additives which are generally used in ordinary formulation.

The carriers and vehicles to be used for the formulation may be solid or liquid, non-toxic pharmaceutically-acceptable substances. As examples, mentioned are lactose, magnesium stearate, starch, talc, gelatin, agar, pectin, Arabic gum, olive oil, sesame oil, cacao butter, ethylene glycol and others which are ordinarily used in the art.

The pharmaceutical composition can be administered either perorally as tablets, pills, capsules, granules, powders, liquids, etc., or parenterally as intravenous or intramuscular injections, suppositories, endermic preparations, inhalants, etc. The dose of the composition is suitably determined for individual patients, depending on their conditions, ages, sexes, etc. In general, however, the peroral dose to adults is approximately from 0.01 mg/kg/day to 100 mg/kg/day, and this is administered at one time or in from 2 to 4 portions. Where the composition is administered intravascularly,- depending on the conditions of patients, its dose is, in general, approximately from 0.001 mg/kg to 10 mg/kg and is applied once to several times a day.

BEST MODES OF CARRYING OUT THE INVENTION

The present invention is described in more detail by means of the following examples. However, the compounds of the present invention are not limited to only the compounds of the examples but include all the compounds of the above-mentioned formula (I), their salts, hydrates, solvates, geometric and optical isomers and polymorphic isomers.

Some starting compounds from which the compounds of the present invention are produced are novel, and the production of such novel starting compounds is demonstrated in the following referential examples.

Referential Example 1:

1.85 g of ethyl 4-oxo-1-piperidine-acetate and 1.1 g of pyrrolidine were dissolved in 50 ml of benzene and refluxed for 24 hours in a Dean-Stark device. The reaction liquid was concentrated, and 50 ml of benzene and 1.7 g of methyl acrylate were added thereto and refluxed for 48 hours. 7 ml of water was added to the reaction liquid and refluxed for further 2 hours, and thereafter the organic layer was separated. This was dried with sodium sulfate and then concentrated, and the resulting residue was purified by silica gel column chromatography (using an eluent of chloroform/methanol=50/1) to obtain 1.8 g of methyl 1-ethoxycarbonylmethyl-4-oxo-3-piperidinepropionate as an oily substance.

Mass spectrum (m/z): FAB (Pos) 272(M$^+$+1) NMR spectrum (CDCl$_3$, TMS internal standard): δ: 1.29 (3H, t), 1.51–1.58 (1H, m), 2.06–2.13 (1H, m), 2.31–2.48 (4H, m), 2.61–2.74 (3H, m), 3.14–3.17 (2H, m), 3.36 (2H, d), 3.66 (3H, s), 4.20 (2H, q).

In the same manner as in Referential Example 1, obtained was a compound of the following Referential Example 2.

Referential Example 2:

Methyl 1-(tert-butoxycarbonylmethyl)-4-oxo-3-piperidinepropionate

Starting compound: Tert-butyl 4-oxo-1-piperidineacetate Mass spectrum (m/z): FAB (Pos) 300(M$^+$+1) NMR spectrum (CDCl$_3$, TMS internal standard): δ: 1.48 (9H, s), 1.50–1.59 (1H, m), 2.05–2.15 (1H, m), 2.30–2.46 (4H, m), 2.60–2.70 (3H, m), 3.13–3.17 (2H, m), 3.25 (2H, d), 3.66 (3H, s).

Referential Example 3:

1.74 g of methyl 1-ethoxycarbonylmethyl-4-oxo-3-piperidinepropionate, 1.2 g of 4-(1-piperazinyl) benzonitrile and 0.8 g of acetic acid were dissolved in 50 ml of dichloromethane, and 2.7 g of sodium triacetoxyborohydride was added thereto and stirred at room temperature for 24 hours. The reaction liquid was neutralized with an aqueous 1N-sodium hydroxide solution and then the organic layer was separated. This was dried with sodium sulfate and concentrated, and the resulting residue was purified by silica gel chromatography (using an eluent of hexane/ethyl acetate=1/1) to obtain 1.1 g of methyl 4-[4-(cyanophenyl)-1-piperazinyl]-1-ethoxycarbonylmethyl-3-piperidinepropionate.

Mass spectrum (m/z): FAB (Pos) 443(M++1) NMR spectrum (CDCl$_3$, TMS internal standard): δ: 1.28 (3H, t), 1.66–1.77 (2H, m), 1.94–1.97 (3H, m), 2.05–2.08 (2H, m), 2.19–2.24 (1H, m), 2.35–2.41 (2H, m), 2.53–2.58 (3H, m), 2.64–2.66 (2H, m), 2.94 (1H, d), 2.99 (1H, d), 3.15 (2H, dd), 3.32–3.36 (3H, m), 3.66 (3H, s), 3.33 (2H, q), 6.85 (2H, d), 7.48 (2H, d).

In the same manner as in Referential Example 3, obtained was a compound of the following Referential Example 4.

Referential Example 4:

Methyl 4-[4-(4-cyanophenyl)-1-piperazinyl]-1-(tert-butoxycarbonylmethyl)-3-piperidinepropionate Mass spectrum (m/z):-FAB (Pos) 471(M++1) NMR spectrum (CDCl$_3$, TMS internal standard): δ: 1.47 (9H, s), 1.64–1.70 (1H, m), 1.75 (1H, d), 1.94–1.99 (3H, m), 2.03–2.09 (2H, m), 2.17–2.22 (1H, m), 2.35–2.42 (2H, m), 2.52–2.58 (3H, m), 2.63–2.67 (2H, m), 2.92–2.97 (3H, m), 3.15 (1H, d), 3.33 (3H, t), 3.66 (3H, s), 6.85 (2H, d), 7.48 (2H, d).

In the same manner as in Referential Example 1, obtained was a compound of the following Referential Example 5.

Referential Example 5:

Tert-butyl 3-(2-methoxycarbonylethyl)-4-oxo-1-piperidinepropionate

Starting Compounds: Tert-butyl 4-oxo-1-piperidinepropionate, and methyl acrylate Mass spectrum (m/z): FAB (Pos) 314(M++1) NMR spectrum (CDCl$_3$, TMS internal standard): δ: 1.46 (9H, s), 1.50–1.59 (1H, m), 2.04–2.13 (1H, m), 2.23 (1H, t), 2.34–2.45 (5H, m), 2.48–2.58 (3H, m), 2.75–2.80 (2H, m), 3.02–3.08 (2H, m), 3.66 (3H, s).

Referential Example 6:

9.65 g of methyl 4-oxo-3-piperidinecarboxylate hydrochloride, 21.0 g of ethyl bromoacetate and 24.0 g of potassium carbonate were dissolved in 200 ml of N,N-dimethylformamide and stirred at room temperature overnight. 100 ml of water was added to the reaction liquid, which was then extracted with 500 ml of ethyl acetate. The resulting extract was dried with sodium sulfate and concentrated. The resulting residue was purified by silica gel column chromatography (using an eluent of chloroform) to obtain 9.0 g of ethyl 3-ethoxycarbonylmethyl-3-methoxycarbonyl-4-oxo-1-piperidineacetate as an oily substance.

Mass spectrum (m/z): FAB (Pos) 330(M++1) NMR spectrum (CDCl$_3$, TMS internal standard): δ: 1.23–1.31 (6H, m), 2.46–2.51 (1H, m), 2.71 (2H, dd), 2.91–2.96 (2H, m), 3.00–3.08 (2H, m), 3.35–3.45 (2H, m), 3.79 (3H, s), 4.10–4.19 (4H, m).

Referential Example 7:

1.0 g of ethyl 3-ethoxycarbonylmethyl-3-methoxycarbonyl-4-oxo-1-piperidineacetate and 140 mg of lithium chloride were dissolved in 10 ml of N,N-dimethylformamide and refluxed for 48 hours. 10 ml of water was added to the reaction liquid, which was then extracted with 100 ml of ethyl acetate. The resulting extract was dried with sodium sulfate and concentrated.

The resulting residue was purified by silica gel column chromatography (using an eluent of chloroform) to obtain 400 mg of diethyl 4-oxo-1,3-piperidinediacetate as an oily substance.

Mass spectrum (m/z): FAB (Pos) 272(M$^+$+1) NMR spectrum (CDCl$_3$, TMS internal standard): δ: 1.23–1.30 (6H, m), 2.18 (1H, dd), 2.36–2.40 (1H, m), 2.50 (1H, t), 2.70–2.77 (3H, m), 3.13–3.26 (3H, m), 3.38 (2H, s), 4.09–4.22 (4H, m).

Referential Example 8:

1.94 g of methyl 4-oxo-3-piperidinecarboxylate hydrochloride, 1.68 g of sodium hydrogencarbonate and 1.67 g of ethyl bromoacetate were dissolved in a mixed solvent comprising 32 ml of water and 8 ml of diethyl ether and stirred at room temperature overnight. 50 ml of ethyl acetate was added to the reaction liquid, and the organic layer was separated by liquid-liquid separation. This was dried with sodium sulfate and concentrated. The resulting residue was purified by silica gel column chromatography (using a gradient eluent of chloroform to chloroform/methanol=100/1) to obtain 1.5 g of ethyl 3-methoxycarbonyl-4-oxo-1-piperidineacetate as an oily substance.

Mass spectrum (m/z): FAB (Pos) 244($M^+$+1) NMR spectrum ($CDCl_3$, TMS internal standard):
δ: 1.29 (3H, t), 2.45–2.47 (2H, m), 2.80 (2H, t), 3.31 (2H, s), 3.36 (3H, s), 3.76 (3H, s), 4.20 (2H, q).

In the same manner as in Referential Example 3, obtained was a compound of the following Referential Example 9 (1) and (2).

Referential Example 9:
(1) Tert-butyl 4-[4-(4-cyanophenyl)-1-piperazinyl]-3-(2-methoxycarbonylethyl)-1-piperidinepropionate Starting compound: Tert-butyl 3-(2-methoxycarbonylethyl)-4-oxo-1-piperidinepropionate Mass spectrum (m/z): FAB (Pos) 485($M^+$+1) NMR spectrum ($CDCl_3$, TMS internal standard): δ: 1.44 (9H, s), 1.53–1.59 (2H, m), 1.75 (1H, d), 1.89–2.05 (5H, m), 2.23–2.77 (11H, m), 2.87 (1H, d), 2.93 (1H, d), 3.32 (2H, d), 3.66 (3H, s), 6.85 (2H, d), 7.48 (2H, d).
(2) (+/−)-cis-diethyl 4-[4-(4-cyanophenyl)-1-piperazinyl]-1,3-piperidinediacetate Starting compound: Diethyl 4-oxo-1,3-piperidineacetate Referential Example 10:
4.0 g of (+/−)-cis-diethyl 4-[4-(4-cyanophenyl)-1-piperazinyl]-1,3-piperidinediacetate and 3.4 g of (+)-dibenzoyl-D-tartaric acid were dissolved in 140 ml of a mixed solvent of ethyl acetate/diisopropyl ether (1/1) and subjected to resolving crystallization. The crystals obtained were recrystallized several times from a mixed solvent of ethyl acetate/diisopropyl ether (1/1), whereby was obtained 690 mg of (+)-cis-diethyl 4-[4-(4-cyanophenyl)-1-piperazinyl]-1,3-piperidinediacetate (+)-dibenzoyl-D-tartrate (98.4% e.e.).
Specific optical rotation ($C_{24}H_{34}N_4O_4$; as a free form): $[\alpha]_D^{25}$=+32.40°c=1.00 ($CHCl_3$)

Referential Example 11:
6.3 g of (+/−)-cis-diethyl 4-[4-(4-cyanophenyl)-1-piperazinyl]-1,3-piperidinediacetate and 5.4 g of (−)-dibenzoyl-L-tartaric acid were dissolved in 180 ml of a mixed solvent of ethyl acetate/diisopropyl ether (1/1) and subjected to resolving crystallization. The crystals obtained were recrystallized several times from a mixed solvent of ethyl acetate/diisopropyl ether (1/1), whereby was obtained 640 mg of (−)-cis-diethyl 4-[4-(4-cyanophenyl)-1-piperazinyl]-1,3-piperidinediacetate (−)-dibenzoyl-D-tartrate (98.4% e.e.).
Specific optical rotation ($C_{24}H_{34}N_4O_4$; as a free form): $[\alpha]_D^{25}$=−31.7°c=1.67 ($CHCl_3$)

Example 1:
550 mg of methyl 4-[4-(4-cyanophenyl)-1-piperazinyl]-1-ethoxycarbonylmethyl-3-piperidinepropionate was dissolved in 20 ml of ethanol, into which hydrogen chloride was made to blow at from −10° C. to −20° C. until saturation. This was heated up to room temperature and stirred overnight, and thereafter the solvent was. removed by distillation. The residue thus obtained was dissolved in 20 ml of ethanol, and 1.0 g of ammonium carbonate was added thereto and stirred at room temperature overnight. The solvent was removed from the reaction mixture by distillation, and the resulting residue was purified by silica gel column chromatography (using an eluent of chloroform/methanol=10/1) to obtain 500 mg of ethyl 4-[4-(4-amidinophenyl)-1-piperazinyl]-1-ethoxycarbonylmethyl-3-piperidinepropionate hydrochloride.

Mass spectrum (m/z): FAB (Pos) 474($M^+$+1) NMR spectrum (DMSO-$d_6$, TMS internal standard): 65: 1.06 (3H, t), 1.17–1.21 (4H, m), 1.40–2.30 (5H, m), 2.44–2.54 (2H, m), 2.87 (1H, m), 3.15 (1H, dd), 3.17 (3H, d), 3.31 (3H, s), 3.36 (3H, brs), 3.42–3.47 (2H, m), 4.03–4.10 (4H, m), 4.34 (1H, t), 7.07 (2H, d). 7.75 (2H, d)

Example 2:
350 mg of ethyl 4-[4-(4-amidinophenyl)-1-piperazinyl]-1-ethoxycarbonylmethyl-3-piperidinepropionate hydrochloride was dissolved in 20 ml of ethanol, and 2.5 ml of an aqueous solution of 1N-sodium hydroxide was added thereto and stirred at room temperature for 5 hours. 2.5 ml of 1N-hydrochloric acid was added to the reaction liquid, from which the solvent was removed by distillation. The resulting residue was purified by HP-20 column chromatography (using a gradient eluent of water to water/ethanol=50/1) to obtain 180 mg of 4-[4-(4-amidinophenyl)-1-piperazinyl]-1-carboxymethyl-3-piperidinepropionic acid hydrochloride.

Mass spectrum (m/z): FAB (Pos) 418($M^+$+1) NMR spectrum (DMSO-$d_6$, TMS internal standard): δ: 1.75 (1H, brs), 2.02–2.09 (2H, m), 2.38–2.45 (2H, m), 2.51–2.64 (2H, m), 3.04 (1H, d), 3.12 (1H, t), 3.56 (2H, brs), 3.76 (2H. d), 4.14 (4H, dd), 7.21 (2H, d), 7.81 (2H, d), 8.87 (2H, s), 9.04 (2H, s)

Example 3:
1.1 g of methyl 4-[4-(4-cyanophenyl)-1-piperazinyl]-1-(tert-butoxycarbonylmethyl)-3-piperidinepropionate and 1 ml of triethylamine were dissolved in 20 ml of N,N-dimethylformamide, into which hydrogen sulfide was bubbled at room temperature until saturation. After this was stirred at room temperature overnight, 200 ml of an aqueous solution of 2N-sodium carbonate was added thereto. Then, this was extracted three times with 150 ml of ethyl acetate. The organic layers were collected, washed with a saturated saline solution, dried with magnesium sulfate and concentrated. The resulting residue was dissolved in 100 ml of acetone, and 0.3 ml of methyl iodide was added thereto, refluxed for 1 hour and concentrated. The residue thus obtained was dissolved in 50 ml of methanol, and 1.5 g of ammonium acetate was added thereto, refluxed for 2 hours and concentrated. The resulting residue was purified by silica gel column chromatography (using an eluent of chloroform/methanol=10/1) to obtain 0.95 g of methyl 4-[4-(4-amidinophenyl)-1-piperazinyl]-1-(tert-butoxycarbonylmethyl)-3-piperidinepropionate hydroiodide.

Mass spectrum (m/z): FAB (Pos) 488($M^+$+1) NMR spectrum (DMSO-$d_6$, TMS internal standard): δ: 1.06 (1H, m), 1.41 (9H, s), 1.73–1.84 (3H, m), 1.90–2.15 (4H, m), 2.26–2.34 (1H, m), 2.85 (2H, d), 3.03 (2H, dd), 3.32–3.43 (10H, m), 3.59 (3H, s), 7.08 (2H, d), 7.72 (2H, d), 8.54 (2H, s), 8.90 (2H, s).

Example 4:
0.45 g of methyl 4-[4-(4-amidinophenyl)-1-piperazinyl]-1-(tert-butoxycarbonylmethyl)-3-piperidinepropionate hydroiodide was dissolved in 50 ml of an aqueous solution of 90%-trifluoroacetic acid and stirred at room temperature for 15 minutes. The reaction mixture was concentrated, and the resulting residue was purified by HP-20 column chromatography (using an eluent of water/methanol=10/1) to obtain 0.32 g of 4-[4-(4-amidinophenyl)-1-piperazinyl]-3-methoxycarbonylethyl-1-piperidineacetic acid trifluoroacetate.

Mass spectrum (m/z): FAB (Pos) 432($M^+$+1) NMR spectrum (DMSO-$d_6$, TMS internal standard): δ: 1.18 (2H, t), 1.76 (1H, brs), 1.86 (1H, brs), 1.99 (2H, s), 2.20 (1H, m), 2.30 (1H, m), 2.42–2.50 (2H, m), 2.61–2.84 (2H, m), 3.33 (2H, brs), 3.44 (2H, brs), 3.63 (3H, s), 4.03 (2H, q), 7.17 (2H, d), 7.80 (2H, d), 9.02 (4H, brs)

In the same manner as in Example 1, obtained were compounds of the following Examples 5 to 7.

Example 5:

Diethyl 4-(4-(4-amidinophenyl)-1-piperazinyl]-1,3-piperidinediacetate hydrochloride Starting compounds: Diethyl 4-oxo-1,3-piperidinediacetate Mass spectrum (m/z): FAB (Pos) 460 ($M^+$+1) NMR spectrum (DMSO-$d_6$, TMS internal standard): δ: 1.18 (6H, t), 1.69–1.83 (3H, m), 2.01–2.33 (5H, m), 2.66–2.87 (3H, m), 3.08–3.23 (4H, m), 4.03–4.33 (4H, m), 7.06 (2H, d), 7.73 (2H, d)

Example 6:

Ethyl 4-[4-(4-amidinophenyl)-1-piperazinyl]-3-methoxycarbonyl-1-piperidineacetate hydrochloride Starting compound: Ethyl 3-methoxycarbonyl-4-oxo-1-piperidineacetate Mass spectrum (m/z): FAB (Pos) 432($M^+$+1) NMR spectrum (DMSO-$d_6$, TMS internal standard): δ: 1.18 (3H, t), 1.67 (1H, d), 2.17 (1H, q), 2.28–2.35 (2H, m), 2.85–2.87 (1H, m), 2.96–3.01 (2H, m), 3.21 (2H, q), 3.57 (2H, s), 4.07 (2H, q), 7.05 (2H, d), 7.75 (2H, d), 8.71 (2H, s), 8.99 (2H, s)

Example 7:

Ethyl 4-[4-(4-amidinophenyl)-1-piperazinyl]-3-(2-ethoxycarbonylethyl)-1-piperidinepropionate hydrochloride Starting compound: Tert-butyl 4-[4-(4-cyanophenyl)-1-piperazinyl]-3-(2-methoxycarbonylethyl)-1-piperidinepropionate Mass spectrum (m/z): FAB (Pos) 488($M^+$+1) NMR spectrum (DMSO-$d_6$, TMS internal standard): δ: 1.15–1.20 (6H, m), 1.34–1.40 (1H, m), 1.69–1.96 (7H, m), 2.19 –2.27 (1H, m), 2.35–2.43 (3H, m), 2.83–2.86 (2H, m), 3.97–4.11 (4H, m), 7.04 (2H, d), 7.74 (2H, d)

In the same manner as in Example 2, obtained were compounds of the following Examples 8 to 10.

Example 8:

4-[4-(4-Amidinophenyl)-1-piperazinyl]-1,3-piperidinediacetic acid hydrochloride

Starting compound: Diethyl 4-[4-(4-amidinophenyl)-1-piperazinyl]-1,3-piperidinediacetate hydrochloride Mass spectrum (m/z): FAB (Pos) 404($M^+$+1) NMR spectrum (DMSO-$d_6$, TMS internal standard): δ: 1.56 (1H, d), 2.01–2.03 (1H, m), 2.55–2.64 (6H, m), 2.82 (3H, brs), 3.20 (2H, brs), 7.11 (2H, d), 7.76 (2H, d), 8.87 (2H, brs), 8.97 (2H, brs)

Example 9:

4-[4-(4-Amidinophenyl)-1-piperazinyl]-3-carboxy-1-piperidineacetic acid hydrochloride Starting compound: Ethyl 4-[4-(4-amidinophenyl)-1-piperazinyl]-3-methoxycarbonyl-1-piperidineacetate hydrochloride Mass spectrum (m/z): FAB (Pos) 390($M^+$+1) NMR spectrum (DMSO-$d_6$, TMS internal standard): δ: 7.08–7.13 (2H, m), 7.75–7.81 (2H, m), 8.75 (2H, brs), 9.01 (2H, d)

Example 10:

4-[4-(4-Amidinophenyl)-1-piperazinyl]-3-(2-carboxyethyl)-1-piperidinepropionic acid hydrochloride Starting compound: Ethyl 4-[4-(4-amidinophenyl)-1-piperazinyl]-3-(2-ethoxycarbonylethyl)-1-piperidinepropionate hydrochloride Mass spectrum (m/z): FAB (Pos) 432($M^+$+1) NMR spectrum (DMSO-$d_6$, TMS internal standard): δ: 1.70–1.72 (1H, m), 1.88–2.00 (2H, m), 2.39–2.46 (3H, m), 2.80 (2H, t), 2.93–3.04 (3H, m), 7.20 (2H, d), 7.81 (2H, d), 8.93 (2H, brs), 9.05 (2H, brs)

Example 11:

660 mg of (+)-cis-diethyl 4-[4-(4-cyanophenyl)-1-piperazinyl]-1,3-piperidinediacetate-(+)-dibenzoyl-D-tartrate was dissolved in 20 ml of ethanol, into which hydrogen chloride was bubbled at from −10° C. to −20° C. until saturation. This was heated up to room temperature and stirred overnight, and thereafter the solvent was removed by distillation. The residue thus obtained was dissolved in 20 ml of ethanol, and 1.0 g of ammonium carbonate was added thereto and stirred at room temperature overnight. The solvent was removed from the reaction mixture by distillation, and the resulting residue was purified by silica gel column chromatography (using an eluent of chloroform/methanol=10/1) to obtain 300 mg of (+)-cis-diethyl 4-[4-(4-amidinophenyl)-1-piperazinyl]-1,3-piperidinediacetate hydrochloride.

Mass spectrum (m/z): FAB (Pos) 460($M^+$+1) NMR spectrum (DMSO-$d_6$, TMS internal standard): δ: 1.18 (6H, t), 1.33 (1H, m), 1.76 (1H, d), 2.02 (1H, m), 2.13 (1H, t), 2.21 (1H, d), 2.77 (1H, d), 2.86 (1H, d), 3.15 (2H, dd), 4.03–4.08 (4H, m), 7.06 (2H, d), 7.73 (2H, d)

Example 12:

280 mg of (+)-cis-diethyl 4-[4-(4-amidinophenyl)-1-piperazinyl]-1,3-piperidinediacetate hydrochloride was dissolved in 10 ml of 1N-hydrochloric acid and refluxed for 48 hours. The reaction liquid was distilled, and the resulting residue was purified by ODS column chromatography (using an eluent of water) to obtain 160 mg of (+)-cis-4-[4-(4-amidinophenyl)-1-piperazinyl]-1,3-piperidinediacetic acid trihydrochloride (98.2% e.e.).

Specific optical rotation:

$[\alpha]_D^{25}$=+31.20°c=0.50 (MeOH) Mass spectrum (m/z): FAB (Pos) 404($M^+$+1) NMR spectrum (DMSO-$d_6$, TMS internal standard): δ: 7.15 (2H, d), 7.82 (2H, d), 8.89 (2H, s), 9.11 (2H, s)

In the same manner as in Examples 11 and 12, obtained was a compound of the following Example 14.

Example 14:

(−)-cis-4-[4-(4-Amidinophenyl)-1-piperazinyl]-1,3-piperidinediacetic acid trihydrochloride (97.3% e.e.) Starting compound: (−)-Diethyl 4-[4-(4-cyanophenyl)-1-piperazinyl]-1,3-piperidinediacetate (−)-cis-dibenzoyl-L-tartrate Specific optical rotation:

$[\alpha]_D^{25}$=−29.00, c=0.50 (MeOH) Mass spectrum (m/z): FAB (Pos) 404($M^+$+1) NMR spectrum (DMSO-$d_6$, TMS internal standard): δ: 7.17 (2H, d), 7.84 (2H, d), 8.90 (2H, s), 9.13 (2H, s)

Example 15-(1):

14.83 g of N-(tert-butoxycarbonyl)glycine was dissolved in 50 ml of tetrahydrofuran, and 13.73 g of 1,1'-carbonylbis-1 H-imidazole was gradually added thereto and stirred at room temperature for 3 hours. 10 g of p-aminobenzonitrile was added thereto and stirred for 3 hours. Then, the solvent was removed by distillation under a reduced pressure. Water was added to the resulting residue, and the crystals thus formed were taken out by filtration, washed with a small amount of ethanol and then dried under a reduced pressure. Thus was obtained 20.5 g of 2-(tert-butoxycarbonylamino)-N-(4-cyanophenyl)acetamide.

Mass spectrum (m/z): FAB(Pos) 276($M^+$+1) NMR spectrum (CDCl$_3$, TMS internal standard): δ: 1.49 (9H, s), 3.92 (2H, d), 5.18 (1H, brs), 7.61 (2H, d), 7.65 (2H, d), 8.59 (1H, brs)

Example 15-(2):

45.5 ml of a solution of 4N-hydrogen chloride/ethyl acetate was added to 10 g of 2-(tert-butoxycarbonylamino)-N-(4-cyanophenyl)acetamide in a closed vessel and stirred for 18 hours. The crystals formed were removed by filtration, washed with ethyl acetate and then dried under a reduced pressure to obtain 7.7 g of 2-amino-N-(4- cyanophenyl)acetamide hydrochloride. 58.8 ml of an aqueous saturated solution of sodium hydrogencarbonate and 20 ml of water were added to 3.7 g of the hydrochloride and stirred for 1 hour. The crystals thus formed were taken out by filtration and dried under a reduced pressure to obtain 2.5 g of 2-amino-N-(4-cyanophenyl)acetamide.

Mass spectrum (m/z): FAB(Pos) 176($M^+$+1) NMR spectrum (CDCl$_3$, TMS internal standard): δ: 1.68 (2H, brs), 3.50 (2H, s), 7.61 (2H, d), 7.74 (2H, d), 9.75 (1H, brs)

Example 15-(3):

1.83 g of 2-amino-N-(4-cyanophenyl)acetamide was dissolved in 90 ml of methylene chloride, and 3.10 g of ethyl 2-(4-oxo-1-piperidine)acetate, 4.4 ml of acetic acid and 8.88 g of sodium triacetoxyborohydride were added thereto in that order and stirred for 1.5 hours. After this was concentrated under a reduced pressure, water and sodium carbonate were added thereto by which the system was made alkaline. Then, the crystals formed were removed by filtration. The crude crystals were dissolved in chloroform and washed with a saturated saline solution. The resulting organic layer was dried with anhydrous sodium sulfate and filtered, and the resulting filtrate was concentrated under a reduced pressure. Ether was added to the resulting residue, and the solid formed was taken out by filtration to obtain 2.82 g of ethyl 4-[N-(4-cyanophenyl)carbamoylmethylamino]-1-piperidineacetate.

Mass spectrum (m/z): APCI+QlMS: 345 NMR spectrum (CDCl$_3$, TMS internal standard): δ: 1.27 (3H, t), 1.50–1.58 (2H, m), 1.67 (1H, brs), 1.88–1.90 (2H, m), 2.23–2.27 (2H, m), 2.49–2.54 (1H, m), 2.95 (2H, m), 3.22 (2H, s), 3.42 (2H, s), 4.18 (2H, q), 7.62 (2H, d), 7.72 (2H, d), 9.69 (1H, brs)

Example 15-(4):

0.52 g of chloroacetyl chloride was gradually added to a solution comprising 1.0 g of ethyl 4-[N-(4-cyanophenyl) carbamoylmethylamino]-1-piperidineacetate, 20 ml of chloroform and 0.69 g of triethylamine, and stirred for 30 minutes. Next, water and an aqueous saturated solution of sodium hydrogencarbonate were added thereto, thereby making this subjected to liquid-liquid separation. The resulting organic layer was concentrated under a reduced pressure. The resulting residue was subjected to silica gel column chromatography (using chloroform/methanol=50/1, v/v) to obtain 1.19 g of ethyl 4-[N-chloroacetyl-N-[N-(4-cyanophenyl)carbamoylmethyl]amino]-1-piperidineacetate.

Mass spectrum (m/z): FAB(Pos) 421($M^+$+1) NMR spectrum (CDCl$_3$, TMS internal standard):

δ: 1.28 (3H, t), 1.80–1.82 (2H, m), 1.97–2.04 (2H, m), 2.38–2.42 (2H, m), 3.03–3.05 (2H, m), 3.25 (2H, s), 3.68–3.75 (1H, m), 4.12 (2H, s), 4.19 (2H, q), 4.22 (2H, s), 7.53 (2H, d), 7.56 (2H, d), 9.01 (1H, brs)

Example 15-(5):

0.5 g of ethyl 4-[N-chloroacetyl-N-[N-(4-cyanophenyl) carbamoylmethyl]amino)-1-piperidineacetate was dissolved in 20 ml of N,N-dimethylformamide, and 0.090 g of sodium hydride (60% in oil) was added thereto and stirred for 4 hours under heat at from 40° C. to 50° C. An aqueous saturated solution of ammonium chloride was added thereto and concentrated under a reduced pressure. Next, water was added thereto, and the crystals formed were taken out by filtration and recrystallized from ethanol to obtain 0.21 g of ethyl 4-[4-(4-cyanophenyl)-2,5-dioxo-1-piperazinyl]-1-piperidineacetate.

Mass spectrum (m/z): FAB(Pos) 385($M^+$+1) NMR spectrum (CDCl$_3$, TMS internal standard): δ: 1.28 (3H, t), 1.70–1.72 (2H, m), 1.85–1.93 (2H, m), 2.36–2.40 (2H, m), 3.05–3.07 (2H, m), 3.24 (2H, s), 4.09 (2H, s), 4.20 (2H, q), 4.39 (2H, s), 4.44–4.51 (1H, m), 7.48 (2H, d), 7.72 (2H, d)

Example 15-(6):

20 ml of dry ethanol was added to 0.21 g of ethyl 4-[4-(4-cyanophenyl)-2,5-dioxo-1-piperazinyl)-1-piperidineacetate, into which hydrogen chloride was bubbled for about 1 hour at −10° C. or lower. This was gradually heated up to room temperature, stirred overnight and concentrated under a reduced pressure. 20 ml of dry ethanol and 1.56 g of ammonium carbonate were added to the resulting residue and stirred for 3 days. The solvent was removed by distillation, and the resulting residue was subjected to silica gel column chromatography (using chloroform/methanol=5/1, v/v) to obtain 0.17 g of ethyl 4-[4-(4-amidinophenyl)-2,5-dioxo-1-piperazinyl]-1-piperidineacetate hydrochloride.

Mass spectrum (m/z): FAB(Pos) 402($M^+$1) NMR spectrum (DMSO-d$_6$, TMS internal standard): δ: 1.20 (3H, t), 1.53–1.55 (2H, m), 1.76–1.80 (2H, m), 2.28–2.32 (2H, m), 2.91–2.93 (2H, m), 3.24 (2H, s), 4.07–4.11 (4H, m), 4.15–4.19 (1H, m), 4.41 (2H, s), 7.65 (2H, d), 7.88 (2H, d), 9.20 (2H, brs), 9.39 (2H, brs)

Example 16:

0.089 g of ethyl 4-[4-(4-amidinophenyl)-2,5-dioxo-1-piperazinyl]-1-piperidineacetate hydrochloride was dissolved in 1 ml of water, and 0.017 g of lithium hydroxide monohydrate was added thereto with cooling with ice. This was stirred for 30 minutes still with cooling with ice, and an aqueous saturated solution of ammonium chloride was added thereto. Next, this was subjected to ODS column chromatography (H$_2$O→H$_2$O/MeOH=3/2, v/v) to obtain 0.027 g of 4-[4-(4-amidinophenyl)-2,5-dioxo-1-piperazinyl]-1-piperidineacetic acid.

Mass spectrum (m/z): FAB(Pos) 374($M^+$+1) NMR spectrum (DMSO-d$_6$, TMS internal standard): δ: 1.85 (2H, m), 2.13–2.19 (2H, m), 3.22 (2H, m), 3.58 (2H, m), 4.11 (4H, brs), 4.44 (3H, brs), 7.66 (2H, d), 7.86 (2H, d), 9.07 (2H, brs), 9.31 (2H, brs)

Example 17-(1):

0.48 g of sodium cyanoborohydride and 0.57 g of acetic acid were added in that order to a mixed solution comprising 1.0 g of ethyl 4-[N-(4-cyanophenyl) carbamoylmethylamino]-1-piperidineacetate, 10 ml of methanol and 2.85 g of chloroacetaldehyde (40%-aqueous solution), and stirred overnight. The solvent was removed by distillation, and chloroform was added to the resulting residue, which was then washed with an aqueous saturated solution of sodium hydrogencarbonate. The resulting organic layer was separated and concentrated under a reduced pressure. The resulting residue was subjected to silica gel column chromatography (using chloroform/methanol=100/1, v/v) to obtain 1.15 g of ethyl 4-[N-(2-chloroethyl)-N-[N-(4-cyanophenyl)carbamoylmethyl]amino]-1-piperidineacetate.

Mass spectrum (m/z): FAB(Pos) 407($M^+$+1)

Example 17-(2):

1.08 g of ethyl 4-[N-(2-chloroethyl)-N-[N-(4-cyanophenyl)carbamoylmethyl]amino]-1-piperidineacetate was dissolved in 30 ml of N,N-dimethylformamide, and 0.18 g of sodium hydride (60% in oil) was gradually added thereto and stirred for 5 hours. An aqueous saturated solution of ammonium chloride was added thereto, the solvent was removed by distillation, and chloroform and an aqueous saturated solution of sodium hydrogencarbonate were added to this, which was thus subjected to liquid-liquid separation. The resulting organic layer was concentrated under a reduced pressure. Ether was added to the resulting residue, and the solid formed was taken out by filtration to obtain 0.43 g of ethyl 4-[4-(4-cyanophenyl)-3-oxo-1-piperazinyl]-1-piperidineacetate.

Mass spectrum (m/z): FAB(Pos) 371(M⁺+1) NMR spectrum (CDCl₃, TMS internal standard): δ: 1.28 (3H, t), 1.65–1.71 (2H, m), 1.83–1.85 (2H, m), 2.24–2.28 (2H, m), 2.35–2.39 (1H, m), 2.91–2.93 (2H, m), 3.01–3.04 (2H, m), 3.22 (2H, s), 3.46 (2H, s), 3.71–3.73 (2H, m), 4.19 (2H, q), 7.49 (2H, d), 7.68 (2H, d)

In the same manner as in Example 15-(6), obtained was a compound of the following Example 17-(3).

Example 17-(3):
Ethyl 4-[4-(4-amidinophenyl)-3-oxo-1-piperazinyl]-1-piperidineacetate hydrochloride Starting compound: Ethyl 4-[4-(4-cyanophenyl)-3-oxo-1-piperazinyl]-1-piperidineacetate
Elementary analysis (as $C_{20}H_{29}N_5O_3$ 1.5 HCl 3 $H_2O$):

|  | C (%) | H (%) | N (%) | Cl (%) |
| --- | --- | --- | --- | --- |
| Theoretical: | 48.41 | 7.41 | 14.11 | 10.72 |
| Found: | 48.44 | 7.06 | 14.31 | 10.92 |

Mass spectrum (m/z): FAB(Pos) 388(M⁺+1) NMR spectrum (DMSO-d₆, TMS internal standard): δ: 1.19 (3H, t), 1.43–1.47 (2H, m), 1.77–1.80 (2H, m), 2.17–2.21 (2H, m), 2.29 (1H, m), 2,87–2.89 (4H, m), 3.19 (2H, s), 3.33 (2H, s), 3.70–3.72 (2H, m), 4.08 (2H, q), 7.65 (2H, d), 7.84 (2H, d), 9.01 (2H, brs), 9.32 (2H, brs)

In the same manner as in Example 16, obtained was a compound of the following Example 18.

Example 18:
4-[4-(4-Amidinophenyl)-3-oxo-1-piperazinyl]-1-piperidineacetic acid Starting compound: Ethyl 4-[4-(4-amidinophenyl)-3-oxo-1-piperazinyl]-1-piperidineacetate hydrochloride Elementary analysis (as $C_{18}H_{25}N_5O_3$ 2.75 $H_2O$):

|  | C (%) | H (%) | N (%) |
| --- | --- | --- | --- |
| Theoretical: | 52.86 | 7.52 | 17.12 |
| Found: | 52.94 | 7.14 | 16.94 |

Mass spectrum (m/z): FAB(Pos) 360(M⁺+1) NMR spectrum (DMSO-d₆+TFA, TMS internal standard): δ: 2.04 (2H, m), 2,31 (2H, m), 3.13 (2H, m), 3.42 (1H, m), 3.59 (2H, m), 3.66 (2H, m), 3.97–4.02 (4H, m), 4.16 (2H, brs), 7.64 (2H, d), 7.88 (2H, d), 9.09 (2H, brs), 9.32 (2H, brs)

In the same manner as in Example 15-(3), obtained was a compound of the following Example 19-(1):

Example 19-(1):
Ethyl 4-[[2-(4-cyanoanilino)ethyl]amino]-1-piperidineacetate Starting compound: 4-[(2-aminoethyl)amino]benzonitrile Mass spectrum (m/z): FAB(Pos) 331(M⁺+1) NMR spectrum (CDCl₃, TMS internal standard): δ: 1.27 (3H, t), 1.43–1.51 (2H, m), 1.55 (1H, brs), 1.88–1.90 (2H, m), 2.23–2.28 (2H, m), 2.47–2.51 (1H, m), 2.91–2.93 (4H, m), 3.19–3.21 (4H, m), 4.16–4.20 (2H, m), 4.91 (1H, m), 6.57 (2H, d), 7.41 (2H, d)

In the same manner as in Example 15-(4), obtained was a compound of the following Example 19-(2):

Example 19-(2):
Ethyl 4-[N-(2-(4-cyanoanilino)ethyl]-N-methoxalyl amino]-1-piperidineacetate Starting compounds: Ethyl 4-[[2-(4-cyanoanilino)ethyl]amino]-1-piperidineacetate and methyloxalyl chloride Mass spectrum (m/z): FAB(Pos) 417 (M⁺+1)

NMR spectrum (CDCl₃, TMS internal standard): δ: 1.23–1.29 (3H, m), 1.67–1.93 (4H, m), 2.20–2.33 (2H, m), 2.87–3.18 (2H, m), 3.22 (2H, s), 3.35–3.60 (5H, m), 3.90 (3H, s), 4.14–4.34 (2H, m), 4.97 (1H, m), 6.55–6.61 (2H, m), 7.38–7.45 (2H, m)

In the same manner as in Example 15-(5), obtained was a compound of the following Example 19-(3):

Example 19-(3):
Ethyl 4-[4-(4-cyanophenyl)-2,3-dioxo-1-piperazinyl]-1-piperidineacetate
Mass spectrum (m/z): FAB(Pos) 385(M⁺+1) NMR spectrum (CDCl₃, TMS internal standard): δ: 1.28 (3H, t), 1.75–1.78 (2H, m), 1.82–1.90 (2H, m), 2.33–2.38 (2H, m), 3.04–3.06 (2H, m), 3.23 (2H, s), 3.63–3.65 (2H, m), 3.97–3.99 (2H, m), 4.20 (2H, q), 4.51–4.57 (1H, m), 7.54 (2H, d), 7.71 (2H, d)

In the same manner as in Example 15-(6), obtained was a compound of the following Example 19-(4).

Example 19-(4):
Ethyl 4-[4-(4-amidinophenyl)-2,3-dioxo-1-piperazinyl]-1-piperidineacetate hydrochloride
Mass spectrum (m/z): FAB(Pos) 402(M⁺+l) NMR spectrum (DMSO-d₆, TMS internal standard): δ: 1.21 (3H, t), 1.61 (2H, m), 1.77 (2H, m), 2.30 (2H, m), 2.94 (2H, m), 3.32 (2H, s), 3.65 (2H, m), 4.00 (2H, m), 4.11 (3H, m), 7.67 (2H, d), 7.91 (2H, d)

In the same manner as in Example 16, obtained was a compound of the following Example 20.

Example 20:
4-[4-(4-Amidinophenyl)-2,3-dioxo-1-piperazinyl]-1-piperidineacetic acid hydrochloride
Mass spectrum (m/z): FAB(Pos) 374(M⁺+1) NMR spectrum (DMSO-d₆, TMS internal standard): δ: 1.63–1.65 (2H, m), 1.84–1.86 (2H, m), 2.36–2.47 (2H, m), 3.07–3.09 (2H, m), 3.18 (2H, s), 3.63–3.65 (2H, m), 3.99–4.01 (2H, m), 4.23 (1H, m), 7.67 (2H, d), 7.86 (2H, d)

In the same manner as in Example 15-(4), obtained was a compound of the following Example 21-(1).

Example 21-(1):
Ethyl 4-[N-chloroacetyl-N-[2-(4-cyanoanilino)ethyl]amino]-1-piperidineacetate
Mass spectrum (m/z): FAB(Pos) 407(M⁺+l) NMR spectrum (CDCl₃, TMS internal standard): δ: 1.28 (3H, t), 1.75–1.77 (2H, m), 1.91–1.98 (2H, m), 2.33–2.37 (2H, m), 3.04–3.06 (2H, m), 3.24 (2H, s), 3.31–3.34 (2H, m), 3.55–3.58 (2H, m), 4.12 (2H, s), 4.19 (2H, q), 5.06 (1H, m), 6.59 (2H, d), 7.41 (2H, d)

In the same manner as in Example 15-(5), obtained was a compound of the following Example 21-(2).

Example 21-(2):
Ethyl 4-[4-(4-cyanophenyl)-2-oxo-1-piperazinyl]-1-piperidineacetate
Mass spectrum (m/z): FAB(Pos) 371(M⁺+1) NMR spectrum (CDCl₃, TMS internal standard): δ: 1.28 (3H, t), 1.67–1.69 (2H, m), 1.83–1.91 (2H, m), 2.31–2.35 (2H, m), 3.03–3.05 (2H, m), 3.22 (2H, s), 3.45–3.47 (2H, m), 3.55–3.57 (2H, m), 4.01 (2H, s), 4.17–4.22 (2H, q), 4.52–4.59 (1H, m), 6.77 (2H, d), 7.53 (2H, d)

In the same manner as in Example 15-(6), obtained was a compound of the following Example 21-(3).

Example 21-(3):
Ethyl 4-[4-(4-amidinophenyl)-2-oxo-1-piperazinyl]-1-piperidineacetate hydrochloride
Mass spectrum (m/z): FAB(Pos) 388(M⁺+1) NMR spectrum (DMSO-d₆, TMS internal standard): δ: 1.20 (3H, t), 1.49–1.51 (2H, m), 1.72–1.77 (2H, m), 2.25–2.29 (2H, m), 2.90–2.92 (2H, m), 3.22 (2H, s), 3.42–3.45 (2H, m), 3.61–3.63 (2H, m), 4.01 (2H, s), 4.07–4.11 (2H, q), 4.24 (1H, m), 7.02 (2H, d), 7.76 (2H, d)

In the same manner as in Example 16, obtained was a compound of the following Example 22.

Example 22:

4-[4-(4-Amidinophenyl)-2-oxo-1-piperazinyl]-1-piperidineacetic acid hydrochloride Mass spectrum (m/z): FAB(Pos) 360(M$^+$+1) NMR spectrum (DMSO-d$_6$, TMS internal standard): δ: 1.57–1.59 (2H, m), 1.87–1.93 (2H, m), 2.55–2.59 (2H, m), 3.15–3.17 (2H, m), 3.25 (2H, s), 3.42–3.44 (2H, m), 3.63–3.65 (2H, m), 4.01 (2H, s), 4.32–4.37 (1H, m), 7.02 (2H, d), 7.79 (2H, d)

The chemical structural formulas of the compounds obtained in the above Examples are set forth below.

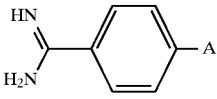

| Example No. | A |
|---|---|
| 1 | 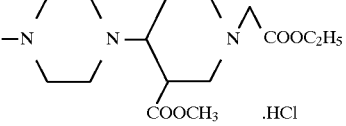 |
| 2 | 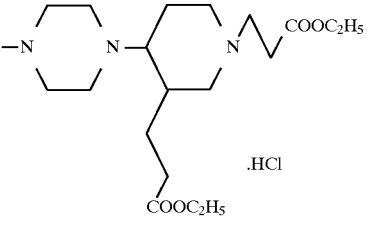 |
| 3 | 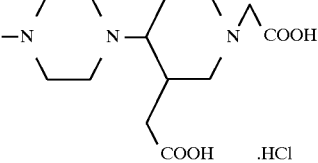 |
| 4 | 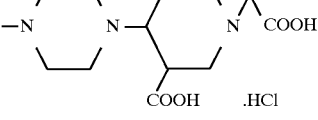 |
| 5 | 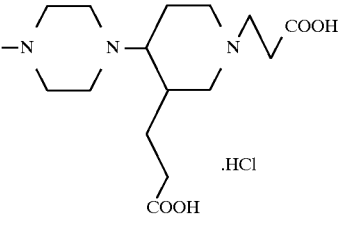 |

-continued

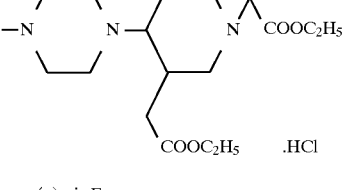

| Example No. | A |
|---|---|
| 6 | 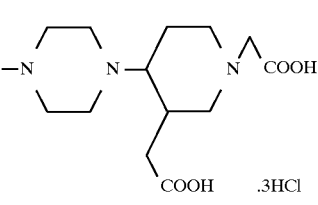 |
| 7 | 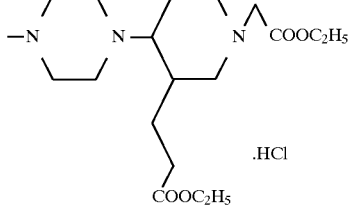 |
| 8 | 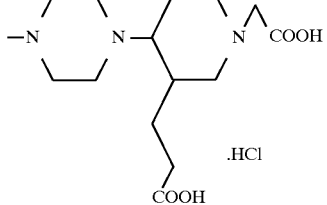 |
| 9 | 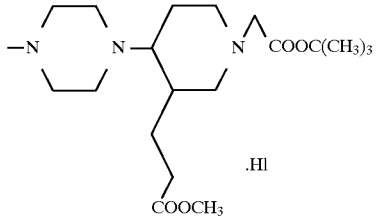 |
| 10 | 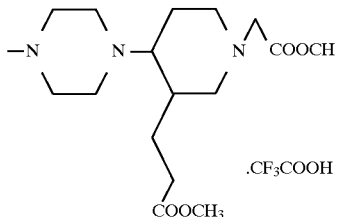 |
| 11 | 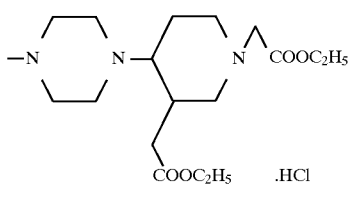 (+)-cis Form |
| 12 | (+)-cis Form |

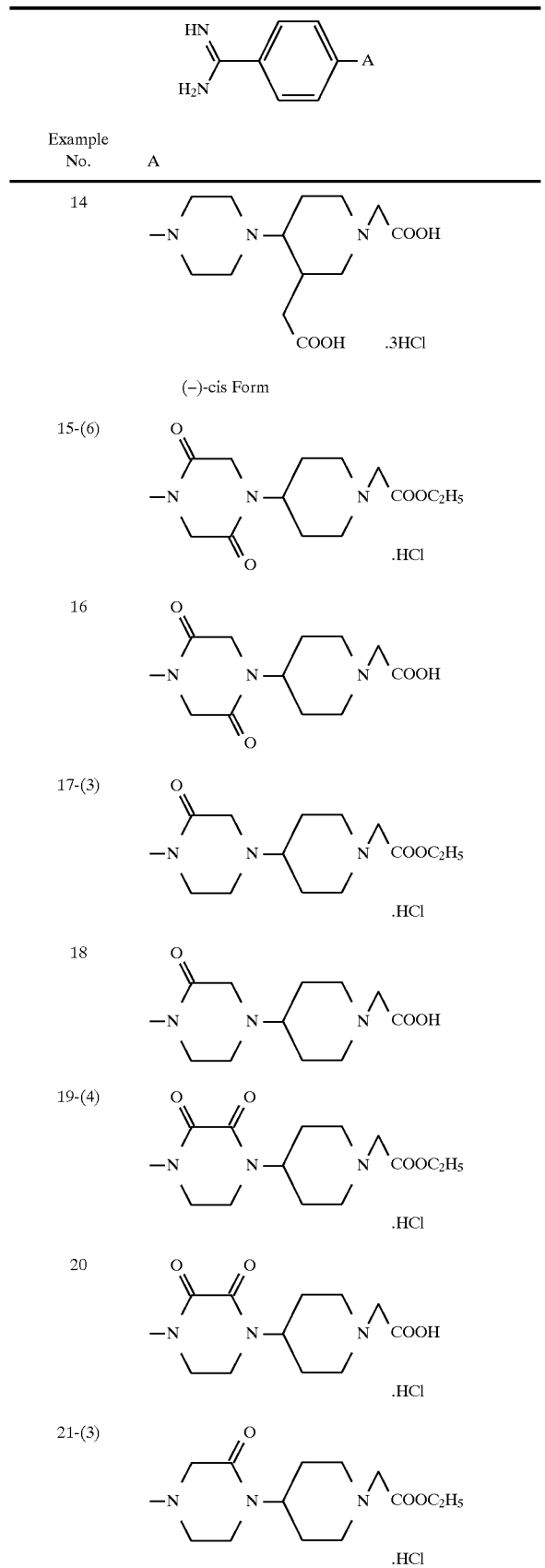

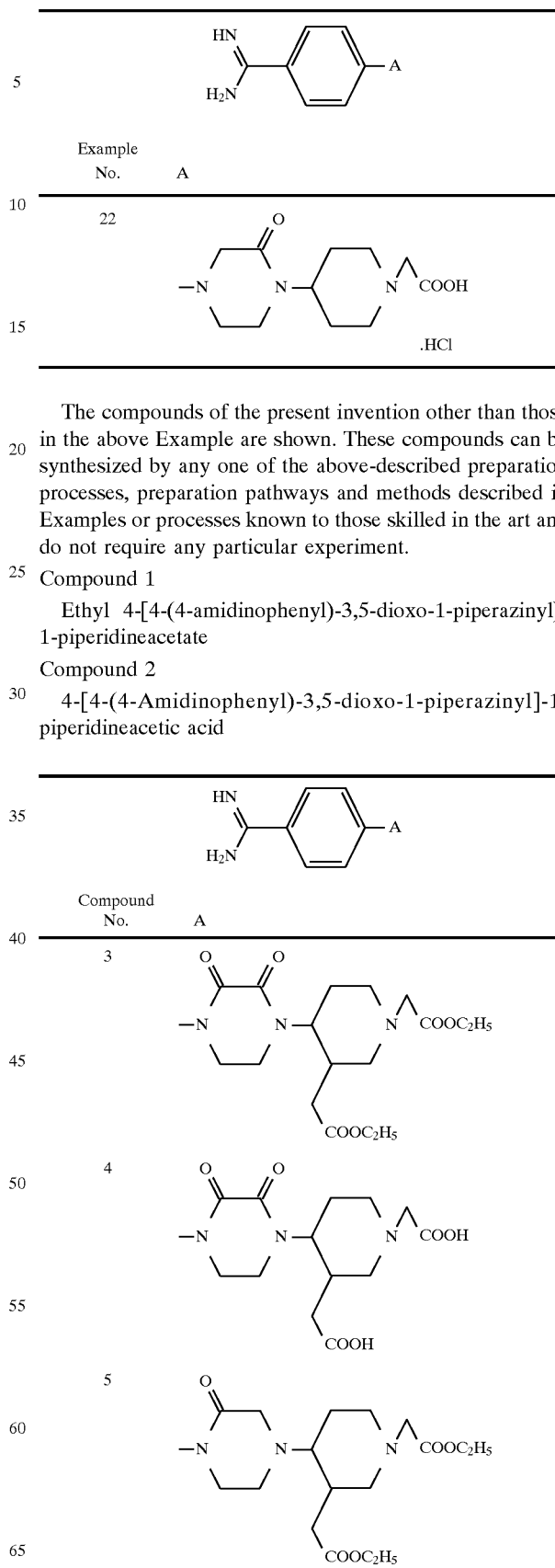

The compounds of the present invention other than those in the above Example are shown. These compounds can be synthesized by any one of the above-described preparation processes, preparation pathways and methods described in Examples or processes known to those skilled in the art and do not require any particular experiment.

Compound 1
  Ethyl 4-[4-(4-amidinophenyl)-3,5-dioxo-1-piperazinyl]-1-piperidineacetate Compound 2
  4-[4-(4-Amidinophenyl)-3,5-dioxo-1-piperazinyl]-1-piperidineacetic acid -continued

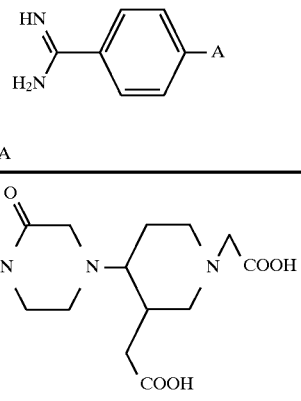

| Compound No. | A |
|---|---|
| 6 | 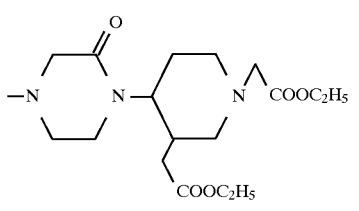 |
| 7 | 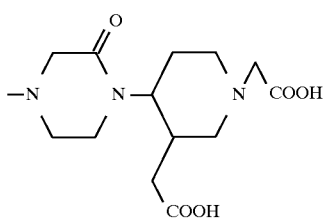 |
| 8 | 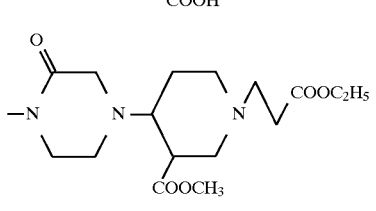 |
| 9 | 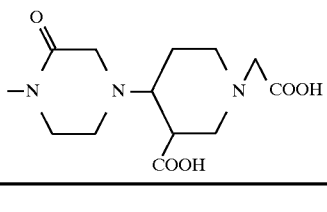 |
| 10 | 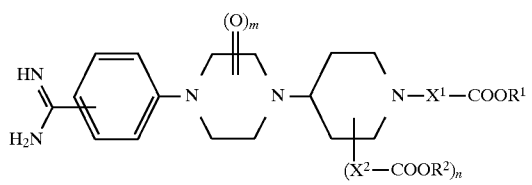 |

We claim:

1. A benzamidine derivative of the following general formula (I), salt thereof, hydrate thereof or solvate thereof:

wherein $R^1$ and $R^2$ are the same or different and each represents a hydrogen atom or an ester residue;
$X^1$ represents a lower alkylene group;
$X^2$ represents a single bond or a lower alkylene group;
m represents 0, 1 or 2;
n represents 0 or 1, provided that n=1 when m=0.

2. The benzamidine derivative, salt thereof, hydrate thereof or solvate thereof claimed in claim 1, wherein $R^1$ and $R^2$ are the same or different and each represents a hydrogen atom, a lower alkyl group, a lower alkenyl group, a lower alkynyl group, a halogeno-lower alkyl group, a cycloalkyl group, a phenyl group, a naphthyl group, an indolyl group, a benzyl group, a lower alkoxy-benzyl group, a nitrobenzyl group, a benzhydryl group, a lower alkoxy-benzhydryl group, a lower alkanoyloxy-lower alkyl group, a lower alkenoyloxy-lower alkyl group, a lower alkanoyl-lower alkyl group, a lower alkenoyl-lower alkyl group, a lower alkoxy-lower alkanoyloxy-lower alkyl group, a lower alkoxy-lower alkenoyloxy-lower alkyl group, a lower alkoxy-lower alkyl group, a lower alkoxy-lower alkoxy-lower alkylalkyl group, a cycloalkyloxycarbonyloxy-lower alkyl group, a lower alkoxycarbonyloxy-lower alkyl group, a lower alkoxy-lower alkoxycarbonyloxy-lower alkyl group, a benzoyloxy-lower alkyl group, a di-lower alkylamino-lower alkyl group, a 2-oxotetrahydrofuran-5-yl group, a 2-oxo-5-alkyl-1,3-dioxolen-4-ylmethyl group, a tetrahydrofuranylcarbonyloxymethyl group or a 3-phthalidyl group.

3. The benzamidine derivative, salt thereof, hydrate thereof or solvate thereof claimed in claim 1, wherein $R^1$ and $R^2$ are the same or different and each represents a hydrogen atom, a lower alkyl group, a lower alkenyl group, a halogeno-lower alkyl group, a lower alkoxy-lower alkyl group, a lower alkoxycarbonyloxy-lower alkyl group, a phenyl group, a benzyl group or a lower alkoxy-benzyl group.

4. The benzamidine derivative, salt thereof, hydrate thereof or solvate thereof claimed in claim 1, wherein $R^1$ and $R^2$ are the same or different and each represents a hydrogen atom or a lower alkyl group.

5. The benzamidine derivative, salt thereof, hydrate thereof or solvate thereof claimed in claim 1, wherein m=0 and n 1.

6. The benzamidine derivative, salt thereof, hydrate thereof or solvate thereof claimed in any of claims 1 to 4, wherein m=1 or 2 and n=0.

7. The benzamidine derivative of claim 1 which is 4-[4-(4-Amidinophenyl)-1-piperazinyl]-1,3-piperidinediacetic acid, an optically-active form thereof, a salt thereof, a hydrate thereof or a solvate thereof.

8. The benzamidine derivative of claim 1 which is (+)-cis-4-[4-(4-Amidinophenyl)-1-piperazinyl]-1,3-piperidinediacetic acid, a salt thereof, a hydrate thereof or a solvate thereof.

9. The benzamidine derivative of claim 1 which is (−)-cis-4-[4-(4-Amidinophenyl)-1-piperazinyl]-1,3-piperidinediacetic acid, a salt thereof, a hydrate thereof or a solvate thereof.

10. The benzamidine derivative of claim 1 which is 4-[4-(4-Amidinophenyl)-2,5-dioxo-1-piperazinyl]-1-piperidineacetic acid, an optically-active form thereof, a salt thereof, a hydrate thereof or a solvate thereof.

11. The benzamidine derivative of claim 1 which is 4-[4-(4-Amidinophenyl)-3-oxo-1-piperazinyl]-1-piperidineacetic acid, an optically-active form thereof, a salt thereof, a hydrate thereof or a solvate thereof.

12. A pharmaceutical composition comprising, as the active ingredient, a benzamidine derivative of the following general formula (I) and a pharmaceutically-acceptable carrier therefor:

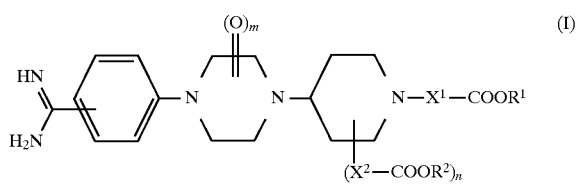

wherein $R^1$ and $R^2$ are the same or different and each represents a hydrogen atom or an ester residue;

$X^1$ represents a lower alkylene group;

$X^2$ represents a single bond or a lower alkylene group;

m represents 0, 1 or 2;

n represents 0 or 1, provided that n=1 when m=0.

13. A pharmaceutical composition as claimed in claim 12, which is a GPIIb/IIIa receptor antagonist.

14. A pharmaceutical composition as claimed in claim 13, wherein the GPIIb/IIIa receptor antagonist is for the treatment and prophylaxis of vascular system disorders as a medicine for ameliorating ischemic cardiac disorders, an adminiculum in cardiosurgery operations or in vascular surgery operations, a medicine for ameliorating cerebrovascular disorders, or a medicine for ameliorating peripheral artery disorders.

15. A method for imparting to a patient GPIIb/IIIa antagonistic activity which comprises administering to the patient a therapeutically effective amount of the pharmaceutical composition of claim 12 containing the benzamidine derivative.

16. The method of claim 15 wherein the benzamidine derivative is 4-[4-(4-Amidinophenyl)-1-piperazinyl]-1,3-piperidinediacetic acid.

17. The method of claim 15 wherein the benzamidine derivative is (+)-cis-4-[4-(4-Amidinophenyl)-1-piperazinyl]-1,3-piperidinediacetic acid.

18. The method of claim 15 wherein the benzamidine derivative is (−)-cis-4-[4-(4-Amidinophenyl)-1-piperazinyl]-1,3-piperidinediacetic acid.

19. The method of claim 15 wherein the benzamidine derivative is 4-[4-(4-Amidinophenyl)-2,5-dioxo-1-piperazinyl]-1-piperidineacetic acid.

20. The method of claim 15 wherein the benzamidine derivative is 4-[4-(4-Amidinophenyl)-3-oxo-1-piperazinyl]-1-piperidineacetic acid.

* * * * *

UNITED STATES PATENT AND TRADEMARK OFFICE
CERTIFICATE OF CORRECTION

PATENT NO. : 5,773,442
DATED : June 30, 1998
INVENTOR(S) : Seijiro Akamatsu, Yuzo Matsumoto, Masato Ichihara,
Tomihisa Kawasaki, Seiji Kaku and Isao Yanagisawa It is certified that error appears in the above-indentified patent and that said Letters Patent is hereby corrected as shown below:

On the title page, item [30] should include:

"June 5, 1995 [JP] Japan...7-137877"

Signed and Sealed this

Eighth Day of December, 1998

Attest:

BRUCE LEHMAN

Attesting Officer  Commissioner of Patents and Trademarks